United States Patent [19]

Sakamoto et al.

[11] Patent Number: 5,263,487
[45] Date of Patent: Nov. 23, 1993

[54] BIOLOGICAL SIGNAL PROCESSING SYSTEM

[75] Inventors: George Sakamoto, Tokyo; Hirotoki Kawasaki, 1-4-8-201, Minamiazabu, Minato-ku, Tokyo, both of Japan

[73] Assignee: Hirotoki Kawasaki, Tokyo, Japan

[21] Appl. No.: 794,526

[22] Filed: Nov. 19, 1991

[30] Foreign Application Priority Data

Nov. 20, 1990 [JP] Japan .................................. 2-315635
Sep. 30, 1991 [JP] Japan .................................. 3-251294

[51] Int. Cl.$^5$ .............................................. A61B 5/04
[52] U.S. Cl. ...................................... 128/731; 128/732
[58] Field of Search ............................... 128/731–732, 128/905

[56] References Cited

U.S. PATENT DOCUMENTS

| | | | |
|---|---|---|---|
| 3,978,847 | 9/1976 | Fehmi et al. | 128/732 |
| 3,993,046 | 11/1976 | Fernandez et al. | 128/732 |
| 4,170,225 | 10/1979 | Criglar et al. | 128/732 X |
| 4,498,080 | 2/1985 | Culver | 128/731 X |
| 4,579,125 | 4/1986 | Strobl et al. | 128/731 |
| 4,649,482 | 3/1987 | Raviv et al. | 128/731 X |
| 4,679,002 | 7/1987 | Sherwin et al. | 128/731 X |

OTHER PUBLICATIONS

Steve Ciarcia "Computers on the Brain" Byte Jul. 1988.

*Primary Examiner*—Kyle L. Howell
*Assistant Examiner*—Jeffrey R. Jastrzab
*Attorney, Agent, or Firm*—McGlew and Tuttle

[57] ABSTRACT

A biological signal processing system for extracting differential signals for alternating signals detected by at least two sensors, and analyzing and processing a plurality of frequency components contained in the differential signals within a predetermined time span, in which a low-pass filter to which the alternating signals are inputted, and a high-pass filter to which the output of the low-pass filter is supplied are provided to extract signals being analyzed having frequencies higher than the cut-off frequency of the low-pass filter and lower than the cut-off frequency of the high-pass filter; the signals being analyzed are sampled; and data signals on the signals being analyzed for every predetermined time span are supplied to a personal computer; the personal computer extracting from the data signals signal components for each of a plurality of frequency components by means of a plurality of digital filters, and visually displaying the signal components for each of the extracted frequency components.

9 Claims, 18 Drawing Sheets

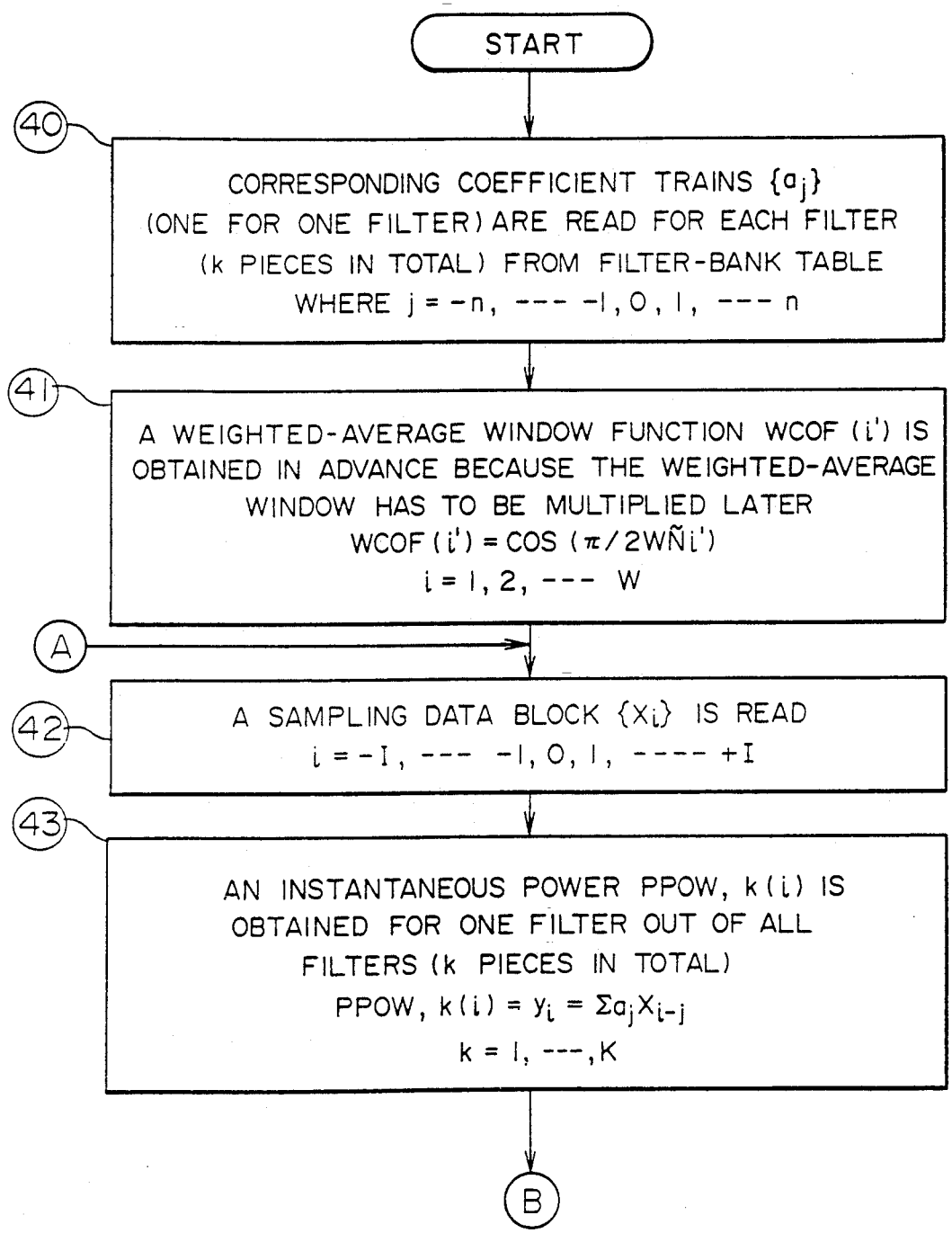

BIOLOGICAL SIGNAL PROCESSING SYSTEM

BACKGROUND OF THE INVENTION

1. Field of the Invention

This invention relates generally to a biological signal processing system for essentially real-time analyzing and displaying biological signals, such as brain waves.

2. Description of the Prior Art

A concept, called biofeedback, is publicly known as an attempt to voluntarily control those functions of a human body which are usually controlled autonomically (involuntarily) or reflexly. That is, successful attempts have been made to inform a subject of the analysis results of brain waves indicating that he (or she) is in a high α-wave intensity and to acquaint him (or her) with his (or her) own conditions at that α-wave intensity so that he (or she) can make efforts to maintain his bodily and mental conditions at a level that can readily induce that state of brain waves has already been put into practical usefulness.

Needless to say, additional benefits associated with the biofeedback technology include;

(1) Fundamental knowledge as to the information necessary to use biological information (2) Clues for changing biological activities by psychological means, and proper orientation to achieve the purpose (3) Encouragement and assistance of help to reinforce learning experience (4) Confirmation by a subject of the information experienced by integrating the information derived from his (or her) own memory and newly perceived from biofeedback signals with the internally perceived information through bodily and mental experience.

This concept has been gradually developed as the argument that the learning technique used for the therapy of the central (voluntary) nervous system can also be applied to the autonomic (involuntary) nervous system was brought forth in the 1960s, and N. E. Miller demonstrated in 1969 that animals can control those functions which had previously been regarded as involuntary.

However, the components of brain-wave signals have heretofore been processed with the fast Fourier transformation (FFT) technique in analyzing brain waves, for example, in real time, as discussed in Steve Ciarcia, "Computers on the Brain" pp. 289-296, "BYTE," July 1988.

FIG. 14 shows the conventional construction of FFT processing. In the figure, reference numeral 1-1 refers to Channel 1 signal; 1-2 to Channel 2 signal; 2 to an FFT processing section; 3 to a square-root reference table; 4 to a sine/cosine reference table; 5-1 to a left-brain power component array; 5-2 to a left-brain phase array; 6-1 to a right-brain power component array; and 6-2 to right-brain phase array, respectively.

The FFT processing section receives the left-brain sample train and the right-brain sample train to perform fast Fourier transformation while referring to the tables 3 and 4 to produce the component arrays 5 and 6 shown in the figure for visual representation, though not shown in the figure.

As shown in FIG. 14, the prior art employs fast Fourier transformation processing. to perform real-time processing, therefore, a relatively large computer has to be used.

SUMMARY OF THE INVENTION

It is an object of this invention to make real-time processing on a small personal computer possible by extracting signals within a required frequency band contained in biological signals and using digital filters.

It is another object of this invention to extract signal components for each of a plurality of frequency components from signals within a required frequency range in biological signals.

It is still another object of this invention to visually display the results of the above-mentioned real-time processing.

It is a further object of this invention to visually display the above-mentioned real-time processing of brain waves out of biological signals.

To achieve these objects, this invention has such a construction that sampled biological signals are fed to a personal computer which in turn extracts signal components for each of a plurality of frequency components with the digital filters thereof, and the results of these processings are visually displayed.

DESCRIPTION OF THE PREFERRED EMBODIMENTS

Figure 1:
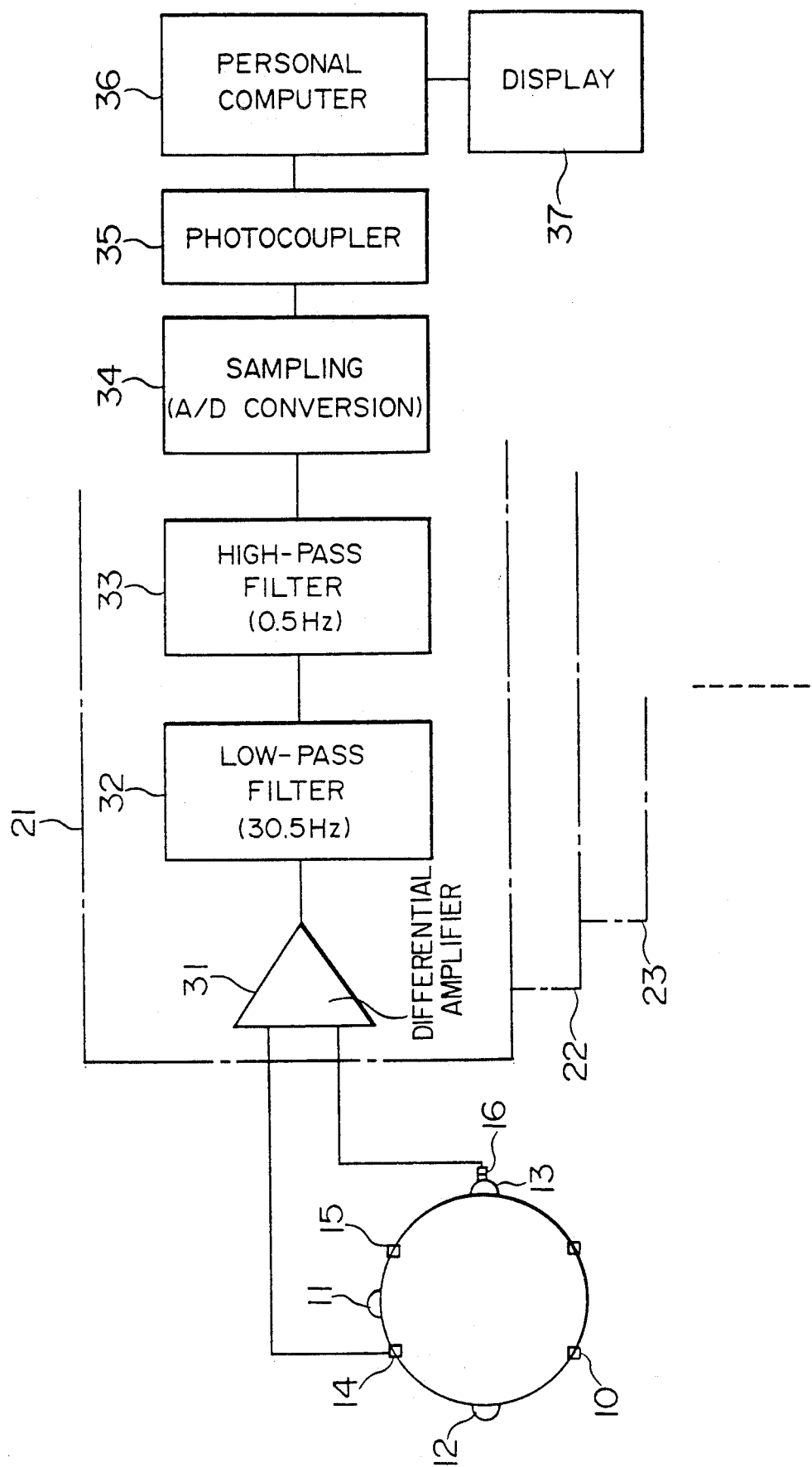
FIG. 1 is a diagram illustrating the basic construction of this invention.

FIG. 1 shows the basic construction of this invention. In the figure, numeral 10 refers to the head of a subject; 11 to the nose; 12 and 13 to the ears; 14, 15, 16, to sensors; 21, 22, 23, to individual sets of units; 31 to a differential amplifier; 32 to a low-pass filter (cut-off frequency: 30.5 Hz); 33 to a high-pass filter (cut-off frequency: 0.5 Hz); 34 to a sampling section; 35 to a photocoupler; 36 to a personal computer; and 37 to a display unit, respectively.

An alternating signal from any one sensor (14, for example) and an alternating signal obtained from the ear are fed to the differential amplifier 31. The low-pass filter 32 and the high-pass filter 33 extract components in a frequency band of 0.5 to 30.5 Hz in the differential signals generated by the differential amplifier 31.

The sampling section 34 samples the extracted signals for A/D conversion. The A/D conversion results are fed to the personal computer 36 via the photocoupler 35 to extract 0.5–1.5-Hz signal components, 1.5–2.5-Hz signal components, - - -, and 29.5–30.5-Hz signal components using digital filters.

In digital filtering by a personal computer, using 30 filters each having a resolution of 1 Hz, processings are executed for 30 dimensions corresponding to $$y_i = \sum_{j=-n}^{n} a_j X_{i-j}$$

to obtain 30 frequency components in 1,830 calculations.

Figure 2:
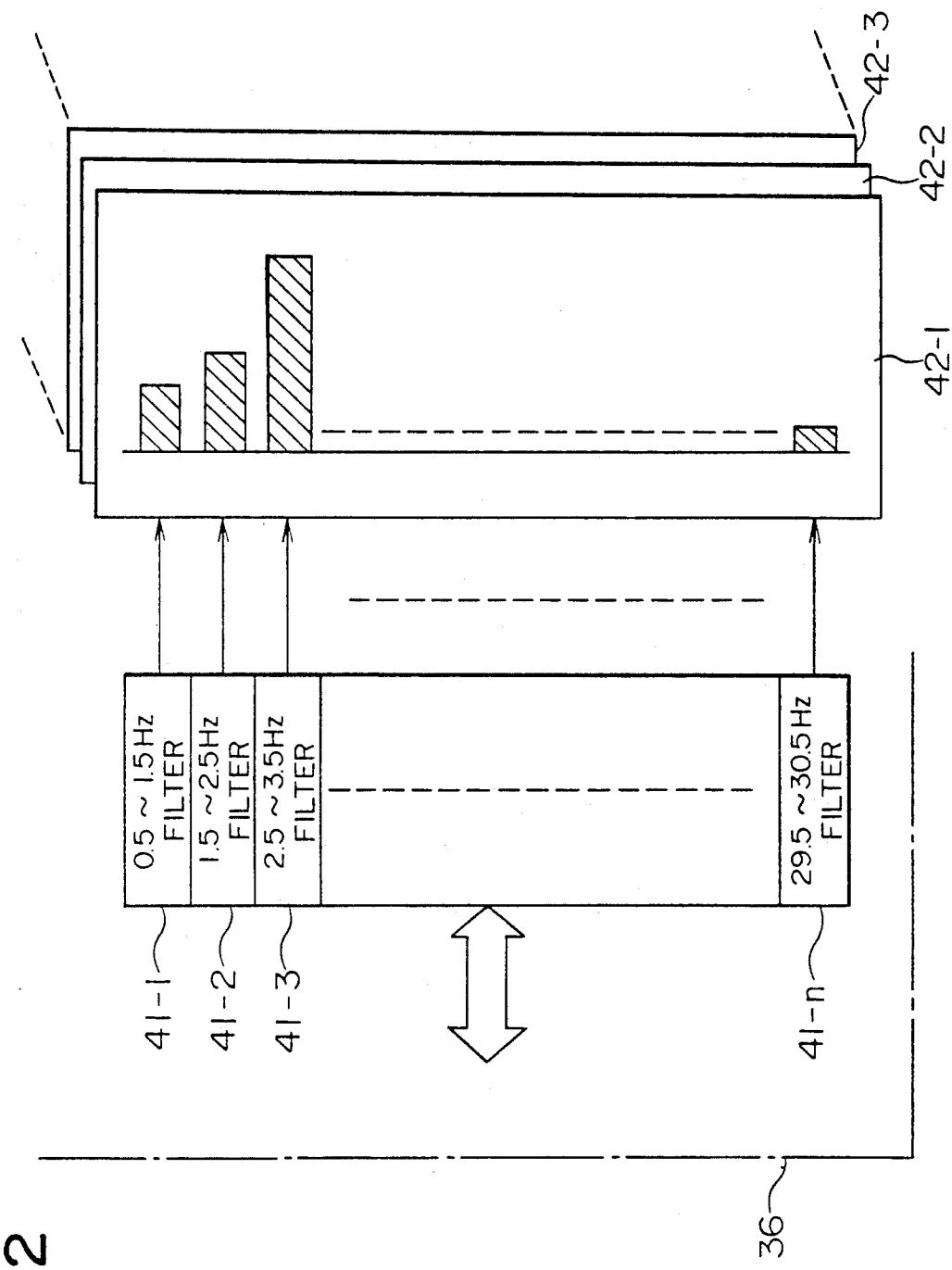
FIG. 2 is a diagram of assistance in schematically explaining processing by the digital filters of this invention.

FIG. 2 is a diagram of assistance in schematically explaining digital filter processing of this invention. In the figure, numeral 36 refers to a personal computer; 41-$i$ to schematically illustrated digital filters having a 1-Hz bandwidth; 42-$i$ to histograms of frequency components for each time span.

In the personal computer as shown in FIG. 1, the processing of dividing the data signals received via the photocoupler 35 into (i) 0.5–1.5-Hz component
(ii) 1.5–2.5-Hz component
(iii) 29.5–30.5-Hz component is performed by means of the band-pass filters 41-1, 41-2, - - -, and 41-n. The data signals are fed once at intervals of 1 second, for example, the 29 frequency components contained in the alternating signals received during an immediately preceding second and are then calculated to display in the histograms 42-$i$ that are continuously displayed for a second on the display unit 37.

If the alternating signals described above are brain waves.

(i) the 0.5–3.5-Hz components are called $\delta$ waves,
(ii) the 3.5–7.5-Hz components are called $\theta$ waves,
(iii) the 7.5–13.5-Hz components are called $\alpha$ waves, and
(iv) the 13.5–30.5-Hz components are called $\beta$ waves.

The state where $\alpha$ waves account for more than 75% of the total is called the $\alpha$ wave-dominant state, the state where $\alpha$ waves account for 50–75% of total is called the $\alpha$ wave-quasidominant state, the state where $\alpha$ waves account for 25–50% of the total is called the mixed $\alpha$-wave state, and the state where $\alpha$ waves account for 0–25% is called the $\alpha$ wave-recessive state. Based on the neurophysiological opinion that the subjective emotional state when $\alpha$ waves are found predominant in brain waves is generally a calm, comfortable and almost buoyant state of mind. It is argued that the brain at that time is in a receptive state, not engaging with any spiritual or emotional activities. In the aforementioned biofeedback, efforts are made to seek and identify the specific desirable emotionally stable state of brain waves for individuals using $\alpha$ waves as a parameter.

Figure 3:
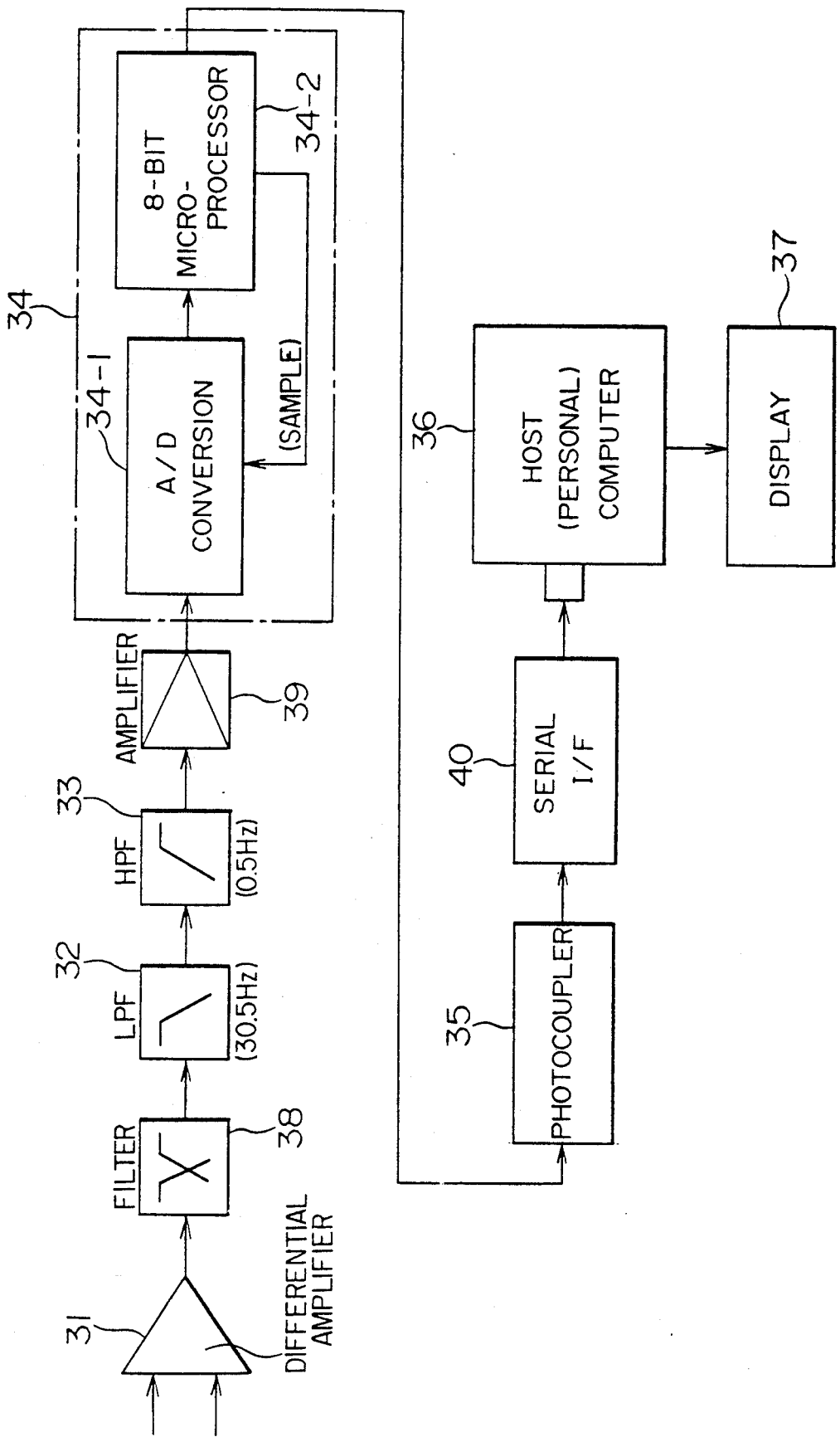
FIG. 3 illustrates the construction of an embodiment of this invention.

FIG. 3 shows the construction of an embodiment of this invention. In the figure, reference numerals 31 through 37 correspond to like numerals in FIG. 1. Numeral 38 refers to a notch filter for eliminating hums from the commercial power source; 39 to an amplifier; 40 to a serial interface section; 34-1 to an A/D converter section; 34-2 to an 8-bit microprocessor for timing sampling.

The personal computer 36 shown in the figure processes only one differential signal from two sensors. In general, however, more than three sensors may be often used, and in such a case, differential signals for each of the signals received from those sensors are processed in a time-sharing mode. A photocoupler 35 in the figure has a function to electrically insulate a system consisting of component elements 31, 38, 32, 33, 39 and 34 from a system consisting of component elements 40, 36 and 37.

The personal computer 36 has a function to inform the subject of the state of $\alpha$ waves using various modes of visual representation on the basis of the separated frequency components.

Figure 4:
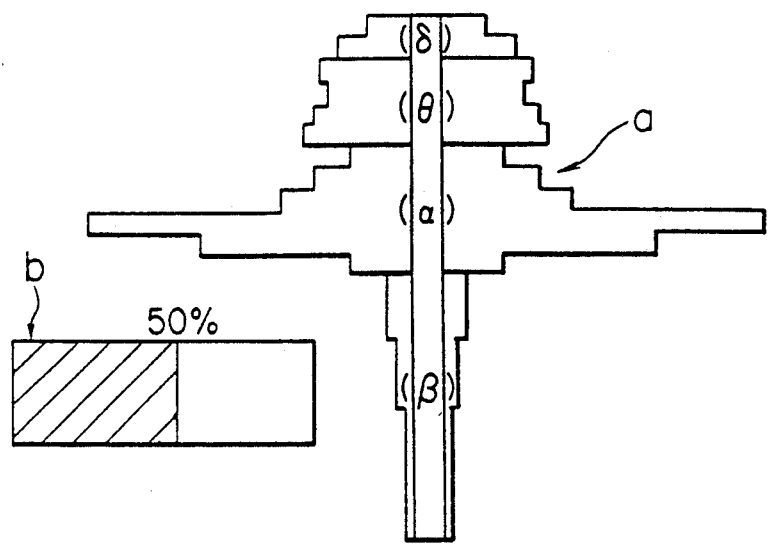
FIG. 4 illustrates examples of the graphical representations of spectral distribution and α-wave ratio.

FIG. 4 shows examples of the graphical representations of spectral distribution and $\alpha$-wave ratio. In the figure, symbol a indicates histograms of frequency components, and symbol b the ratio of $\alpha$ waves to the total, expressed in percentage. Assuming that the personal computer receives data signals at a rate of once a second, any one of the graphical representations shown in FIG. 4 is displayed continuously for one second while changing to the other graphical representation at a rate of once a second. As $\alpha$ waves reach 50, for example, the subject is informed of the fact by audible signals.

Figure 5:
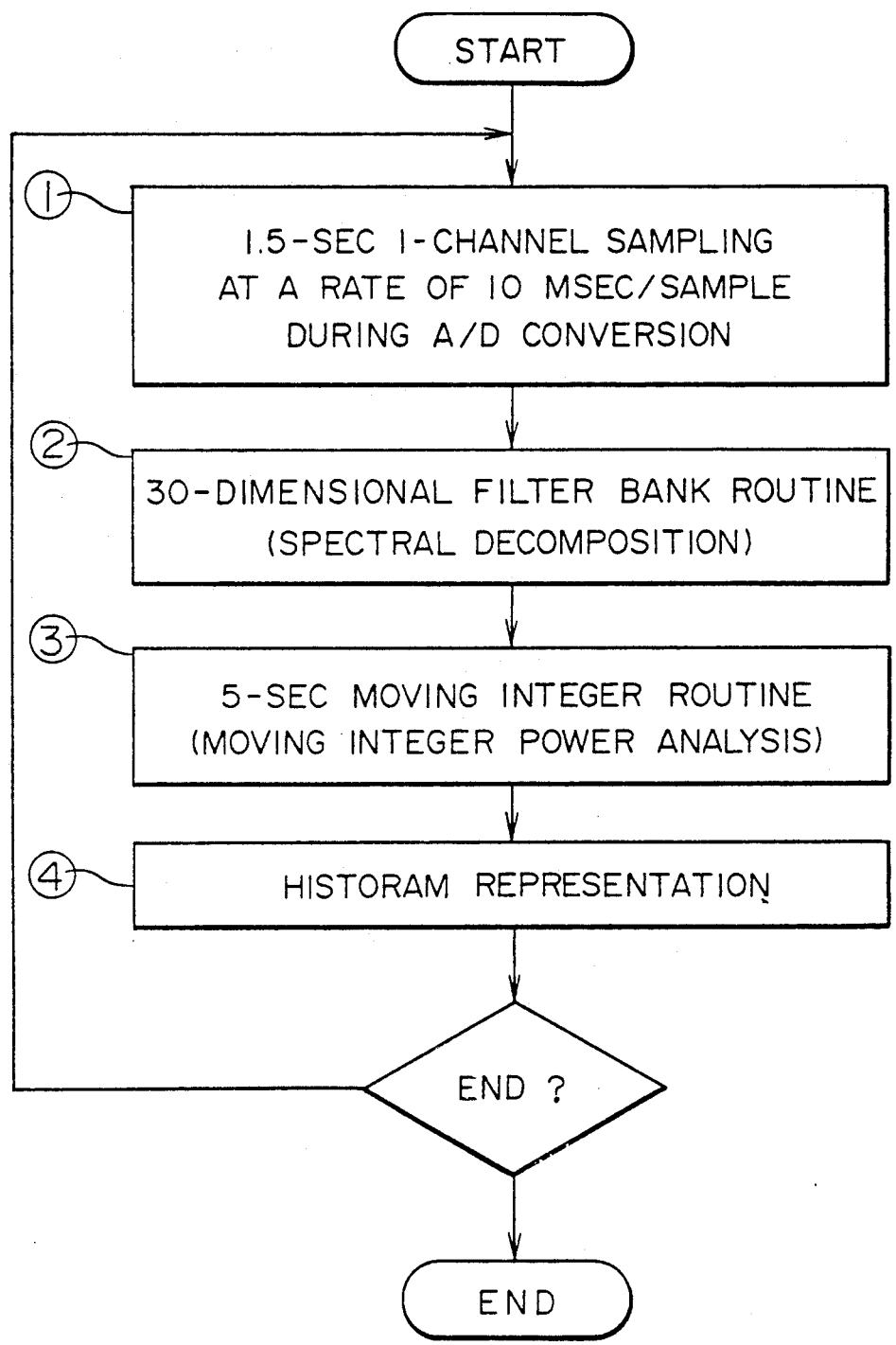
FIG. 5 is a flow chart for displaying the graphical representations shown in FIG. 4.

FIG. 5 is a flow chart for displaying the examples shown in FIG. 4.

Processing (1): Sampling is performed every 10 msec in A/D conversion.
Processing (2): Spectral decomposition is performed.
Processing (3): Moving integral routine is processed.
Processing (4): Histogram representation is performed.

Processings (2) and (3) will be more specifically described later.

Figure 6:
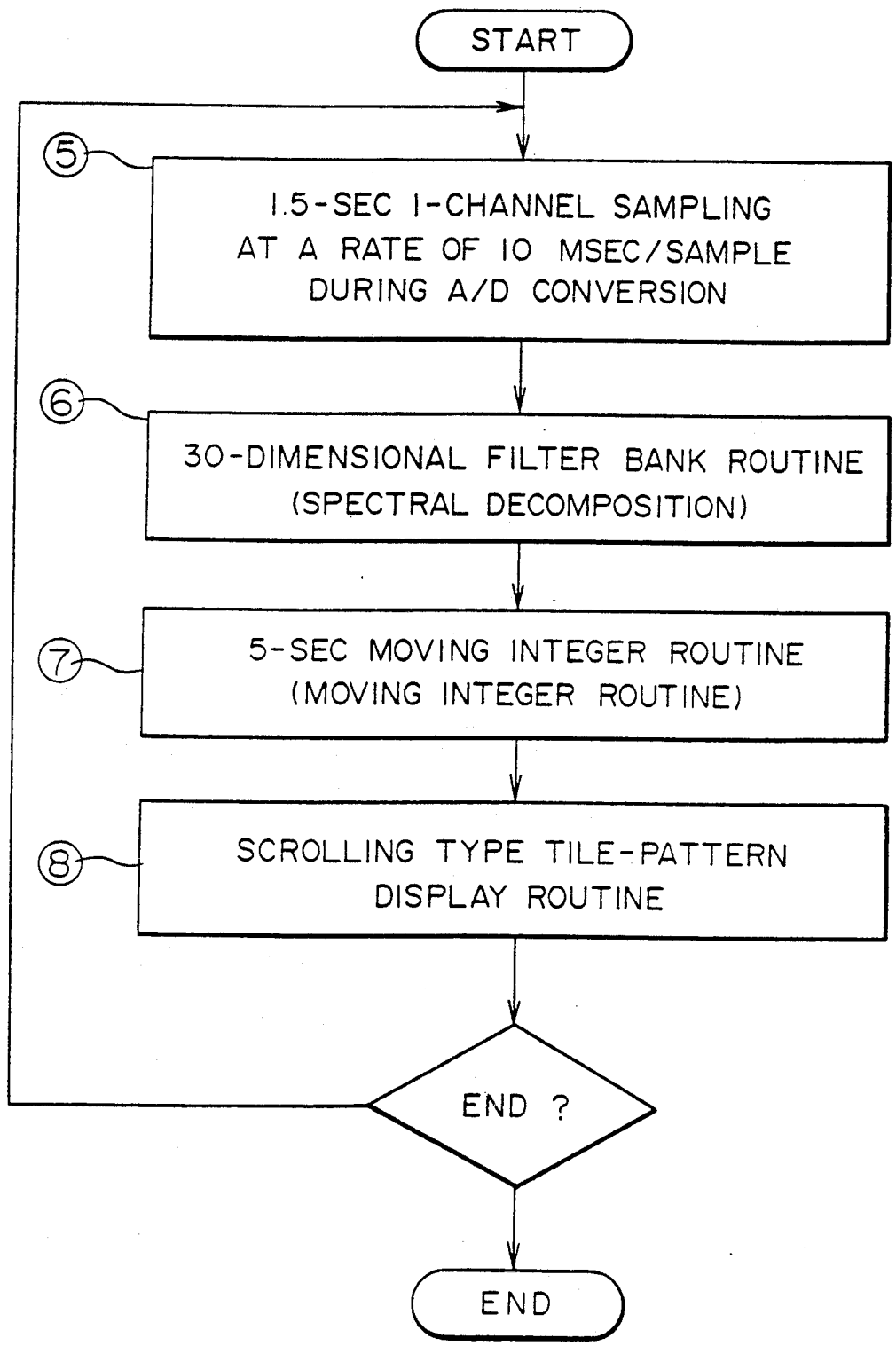
FIG. 6 is a flow chart for displaying the graphical representation of time series spectral distribution.

FIG. 6 is a flow chart for displaying an example of a time-series representation of spectral distribution. A horizontal axis indicates time, and a vertical axis indicates frequency components. The intensities of specific frequency components at specific time are represented by 8-grade colors. This example can display the state in which the intensities of frequency components vary with time.

Processing (5): Sampling is performed every 10 msec in A/D conversion.
Processing (6): Spectral decomposition is performed.
Processing (7): Moving integral routine is processed.
Processing (8): The tile-pattern representation as shown in FIG. 6 is displayed.

Figure 7:
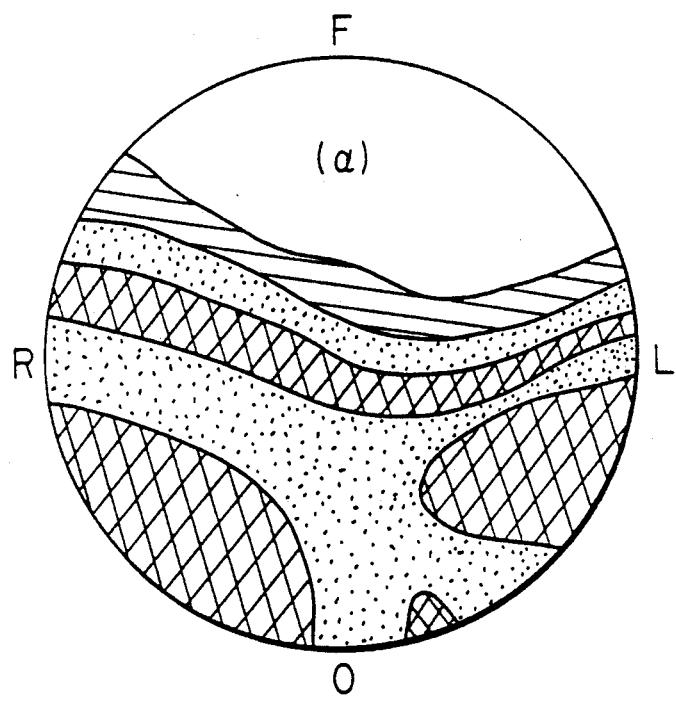
FIG. 7 shows an example of topographical representation.

FIG. 7 shows an example of topographical representation. The topographical representation generally indicates from what positions on the cross-section of a head $\delta$, $\theta$, $\alpha$ and $\beta$ waves are emitted heavily. The state shown in FIG. 7 indicates the position from which $\alpha$ waves are emitted heavily. F in the figure represents the front, R the right side, L the left side, and O the rear of the head. In the example shown in FIG. 7, $\alpha$ waves are emitted heavily from the white-colored area, that is, the front part of the head.

To obtain the representation shown in FIG. 7, a plurality of sensors are disposed around the head, and the state of points on the cross section is calculated on the basis of the output from each sensor.

Figure 8:
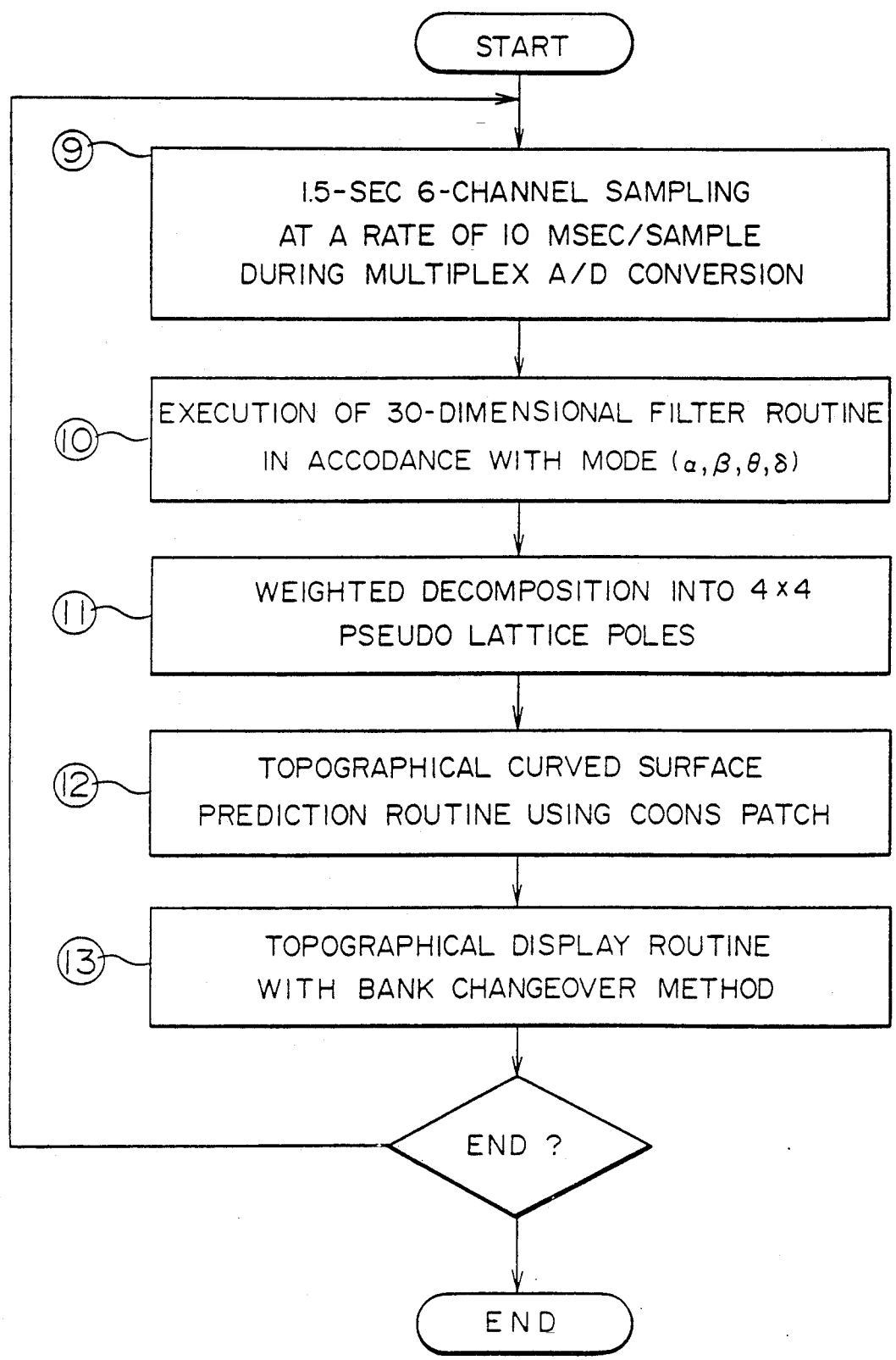
FIG. 8 is a flow chart for displaying the topographical representation shown in FIG. 8.

FIG. 8 is a flow chart for displaying the example shown in FIG. 7.

Processing (9): Signals of 6 channels are sampled every 10 msec in A/D conversion.

Processing (10): Filter processing is performed.

Processing (11): Weighted decomposition processing is performed corresponding to the points on the cross section of the head shown in FIG. 7.

Processing (12): Topographic curved surface prediction routine based on the Coons patch is performed.

Processing (13): Topographic representation is performed.

Because brain waves are a very low potential phenomenon, 50 Hz (60 Hz) and other strong noises have heretofore posed obstacles to obtaining small-sized, low-priced products.

In particular, the difficulty in the analog processing of brain waves for frequency analysis due to low frequency properties of brain waves has long been known. Because of the progress of computer technology, however, the digital processing of brain waves has been developed and put into practical usefulness.

The difficulty in achieving small-sized and low-priced products can be summarized in the following two points:

(1) The conventional methods, such as FFT, might increase statistical errors without an amplifier having good S/N ratio, making it difficult to obtain true values.

(2) The conventional methods impose too much overhead on the CPU, making frequency analysis using the personal computer impractical.

To solve these two problems, this invention proposes the FIR (finite impulse response) filter bank method. This method will be summarized in the following.

(I) FIR filter $$y_i = \sum_{j=-n}^{n} a_j x_{i-j}$$

By appropriately determining $a_j$ ($j = -n, n$) in the above equation in accordance with the properties (frequency characteristics) of the filter and letting it interact with a time series $\{x_i\}$, a time series $\{y_i\}$ having the properties of the filter is produced from the time series.

(II) Frequency analysis

Since the FIR filter is used in the same manner as with normal FETs, 30 filters for separating frequency components for every 1 Hz; that is, for 0.5 Hz, 1.5 Hz, - - - 29.5 Hz, for example, are produced. Producing these filters requires determining a coefficient train best fit to the properties of the filter. That is, determining a coefficient train for producing a filter.

The 30 FIR filters obtained from the algorithm are a block called the filter bank. The frequency-component spectrum obtained with this filter bank is an instantaneous power spectrum. Consequently, a normal frequency analysis, such as the FFT method, can be performed with this filter bank by using the interval integral calculus. The use of this method allows high-quality frequency analysis, such as the FFT method, to be performed with digital processing only from brain waves and other data having poor S/N ratio. In fact, satisfactory operation with an S/N ratio of up to 60 dB is guaranteed with the filter bank used in this system. Frequency analysis can be performed with a small CPU as used in a personal computer by producing a filter bank for the filters needed to obtain desired frequency components, and determining the width of interval integral calculus taking into account overhead on the CPU (in determining the width, the integral using a window function is employed to allow for the effects of width on accuracy).

In the following, embodiments will be described more specifically. First, processing in the embodiments shown in FIGS. 4, 5, and 6 will be described.

Figure 9:
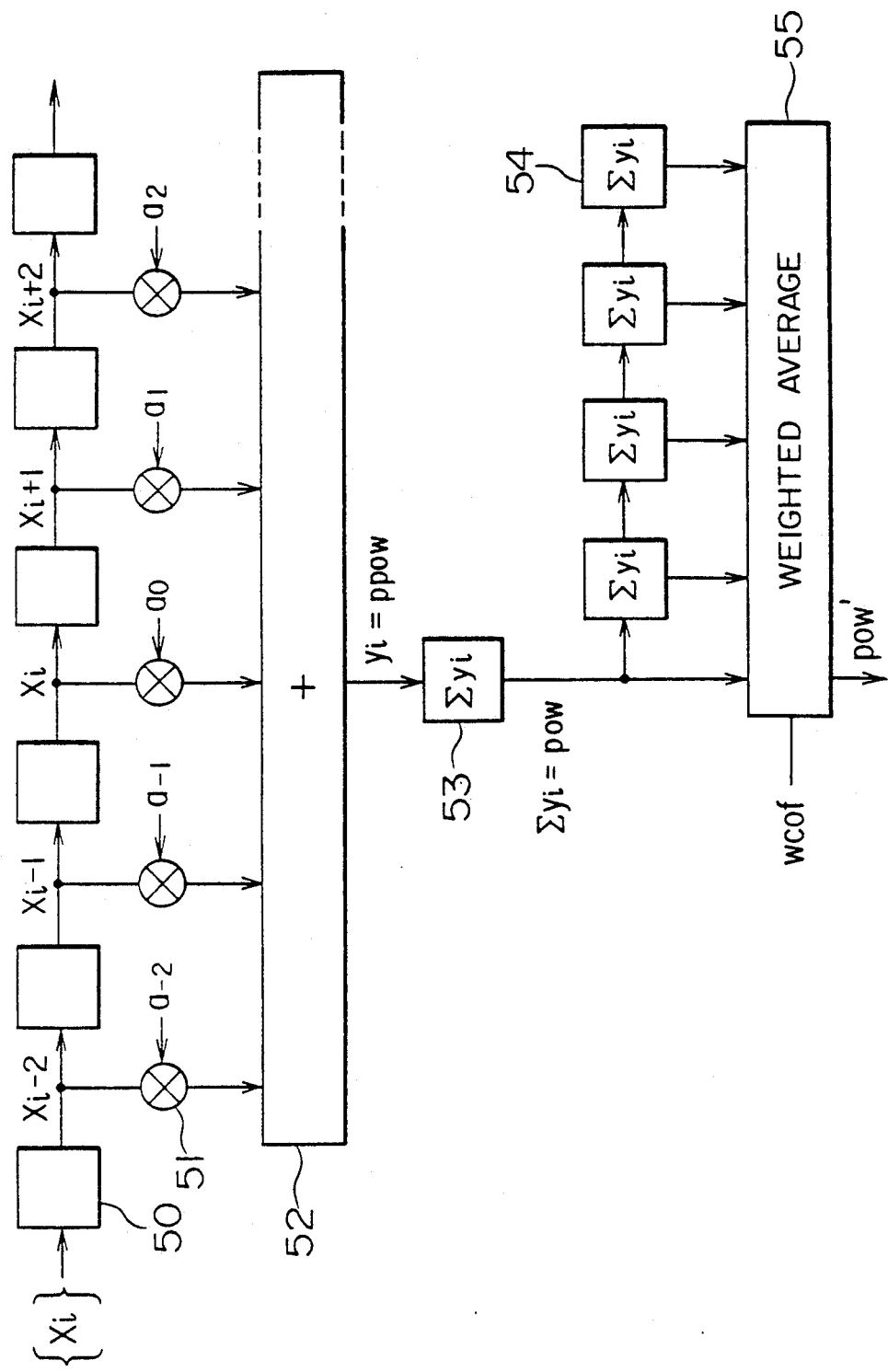
FIG. 9 is a diagram illustrating the construction of digital filters.

FIG. 9 shows the construction (concept) of the digital filter. The digital filter shown in the figure corresponds with a 1-Hz width (components ranging from 0.5 Hz to 1.5 Hz), and a total of k pieces (k=30, for example) of the digital filters are provided. The input of this digital filter is data signals sampled from signals received from the sensor, and the output thereof is signals of the desired frequency components that were extracted with that filter.

In the digital filter shown in the figure, 30 pieces of the unit delay elements 50 are provided, and multipliers 51 corresponding to each of the unit delay elements 50 to receive the output thereof are also provided. A sampling-data block $\{x_i\}$ is inputted into the series-connected unit delay element 50 from an end of the multiplier 51. A coefficient train $\{a_j\}$ corresponding to a given 1-Hz width (that is, corresponding to this FIR filter) is inputted into the multiplier 51 from a filter-bank table. Thus, k pieces of coefficient trains $\{a_j\}$ exist.

Assuming that sampling is performed at intervals of 10 msec, i represents any of integers from 1 to 100. That is, $\{x_i\}$ consists of 100 pieces of sampling data from $x_1$ to $x_{100}$, or data within a predetermined 1-sec ($=10$ msec$\times 100$) period. And, the delay time in the unit delay element 50 becomes 10 msec. One coefficient train $\{a_j\}$ is, on the other hand, equal to the number of the multipliers 51, 30 coefficients, for example. The value of the coefficient to be inputted into each of the multipliers 51 is determined in advance and fixed. The multiplier 51 outputs at every 10 msec the product of the output from the unit delay element 50 at that timing and the coefficient inputted into the multiplier 51.

The adder 52 is used to obtain the sum $y_i$ of the outputs from 30 multipliers 51. $y_i$ is obtained at every 10 msec. $y_i$ here is expressed by the following equation;

$$y_i = \sum_{j=-n}^{n} a_j x_{i-j}$$

and is equivalent to an instantaneous power spectrum ppow.

The integrator 53 is used to obtain $\Sigma y_i$ by integrating the output $y_i$ of the adder 52. The $\Sigma y_i$ is equal to the power pow in a predetermined period. $\Sigma$ here is a power pow within a predetermined 1-sec period in which an inputted sampling-data block $\{x_i\}$ is sampled. That is, the output $y_i$ of the adder 52 is, as a rule, integrated for 1 sec.

In this integration, however, the following points are taken into account. In a predetermined period from the start to the end of inputting $\{s_i\}$, the outputs of several unit delay elements 50 become "0". At the time when only the first one piece of data $x_1$, for example, among $\{x_i\}$ is inputted, data are not inputted into the remaining 29 unit delay elements 50, except the first unit delay element 50. Such a period is 300 msec ($=10$ msec$\times 30$) from the start and the end of input of $\{x_i\}$. Thus, this period is excluded when obtaining the power pow. Consequently, $\Sigma y_i$ is expressed by $$\Sigma_{yi} = \sum_{i=din}^{(2l+1)-din} y_i$$

where $(2l+1)$ is the entire sampling period (1 sec, that is, $l=100$), and din is an invalid period (300 msec, that is, $i=30$) of the start and end of input of $\{x_i\}$.

The register 54 sequentially shifts and holds the $\Sigma_{yi}$ obtained by the integrator 53. In the embodiment shown in the figure, four units, for example, of the register 54 are provided. Assuming that the output of the integrator 53 is the $\Sigma_{yi}$ at the present moment, the four registers 54, starting from the left, sequentially hold the $\Sigma_{yi}$ values 1 second before, 2 seconds before, 3 seconds before, and 4 seconds before, respectively $\Sigma_{yi}$ is shifted every 1 second. As a result, the processing results of sampling data for 5 seconds are held in the registers 54.

The weighted-average arithmetic section 55 performs weighted-average arithmetic on (five pieces of) the $\Sigma_{yI}$=pow obtained sequentially in terms of time for storage in the data-block buffer for windows. The inputs of the weighted-average arithmetic section 55 are the outputs $\Sigma_{yi}$ (five pieces) from the integrator 53 and the four registers 54, with the output thereof being the present power pow'. The weighted-average window function wcof is expressed by $$wcof(i') = \cos\left(\frac{\pi}{2w} i'\right)$$

and can be obtained in advance. Consequently, the power pow' at the present moment is such that the present output $\Sigma_{yi}$=pow of the integrator 53 is corrected by the weighted average after allowing for the $\Sigma_{yi}$ 4 seconds before. With this, unwanted minute oscillation in the power pow' at the present moment is prevented. i' in the equation is any of integers from 1 to 5 because the embodiment shown in the figure covers five (5 sec) $\Sigma_{yi}$.

Figure 10B:
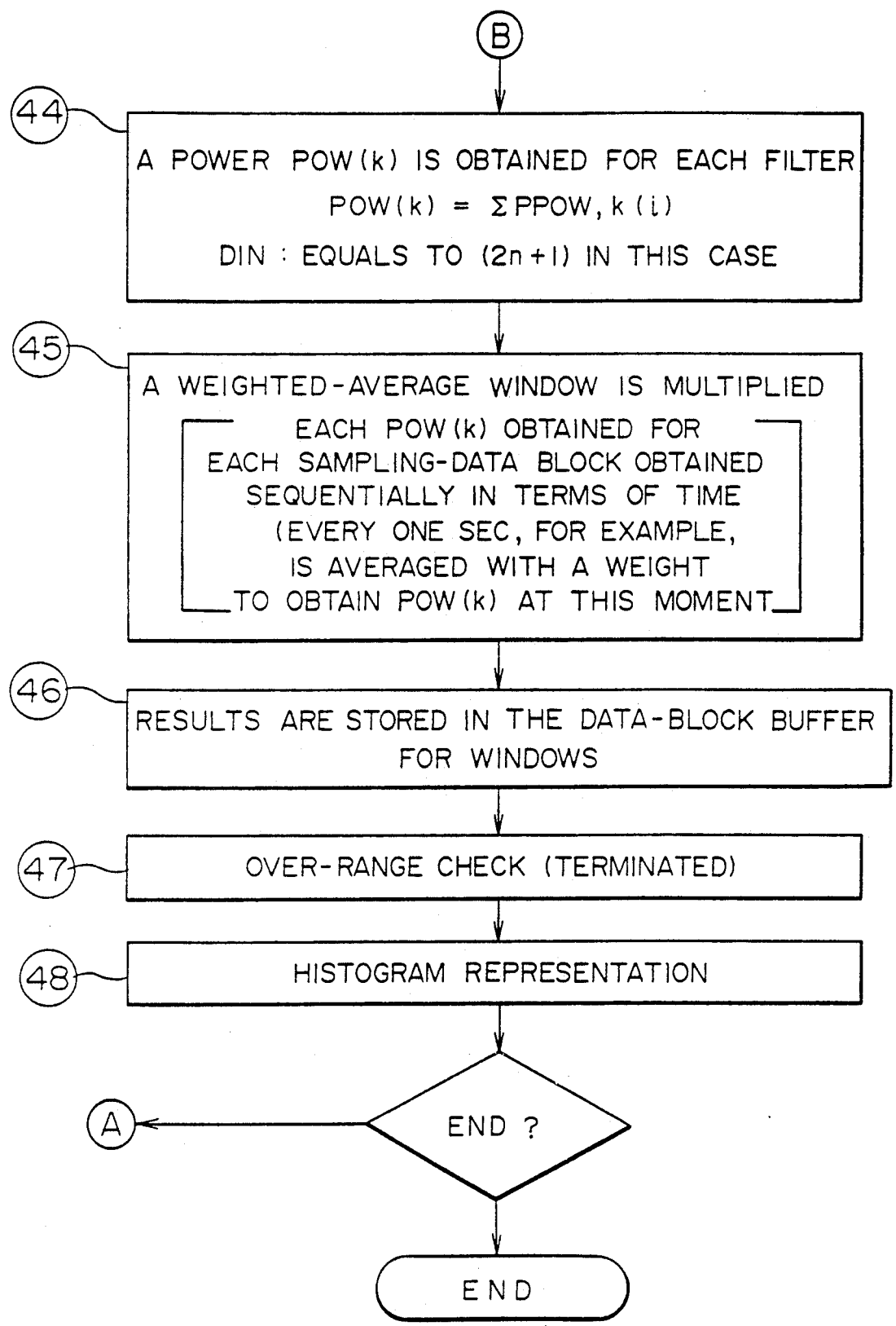
FIGS. 10 A-B are a flow chart for displaying histograms.

FIG. 10 is a flow chart more specifically illustrating Processings (4) and (4) in FIG. 5, which is a flow chart for displaying the histograms shown in FIG. 4. Operations corresponding to the flow chart in FIG. 10 are for accomplishing the operations for the construction shown in FIG. 9.

Processing (40): A coefficient train $\{a_j\}$ corresponding to each of k pieces of digital filters is read from the filter-bank table.

Processing (41): A weighted-average window function wcof (i') is obtained in advance to prepare for the subsequent multiplication of weighted-average windows (Processing (45)). The wcof (i') here is given by $$wcof(i') = \cos\left(\frac{\pi}{2w} i'\right)$$

Processing (42): A sampling-data block $\{x_i\}$ is read.
Processing (43): The instantaneous power ppow, $k(i)=y_i$ for one digital filter (expressed as $k(i)$) among k pieces of digital filters is obtained. The ppow, $k(i)$ is given by $$ppow, k(i) = y_i = \sum_{j=-n}^{n} a_j x_{i-j}$$

Processing (44): the power of the digital filter $k(i)$ is obtained. The pow(k) is given by $$pow(k) = \sum_{i=din}^{(2l+1)-din} ppow, k(i)$$

Processing (45): The power pow is multiplied by the weighted-average window. That is, the power pow'(k) at the present moment is obtained by averaging with a weight the pow(k) obtained corresponding to the sampling-data block $\{x_i\}$ obtained sequentially in terms of time.

Processing (46): The pow'(k) at the present moment is stored in the data-block buffer for windows.

Processing (47): The stored pow'(k) is checked for over range, and if it exceeds the maximum displayable value, the pow'(k) is terminated at that maximum value.

Processing (48): Based on the pow'(k), the histograms of 1-Hz widths (of 1-Hz–2 Hz components, for example) corresponding to the digital filter $k(i)$ at the present moment are displayed.

Then, all the digital filters are checked to see if the processing of them is completed, and if not completed, the operations in Processing (42) and thereafter are repeated.

Next, the processings in the embodiment shown in FIGS. 7 and 9 will be described.

Figure 11:
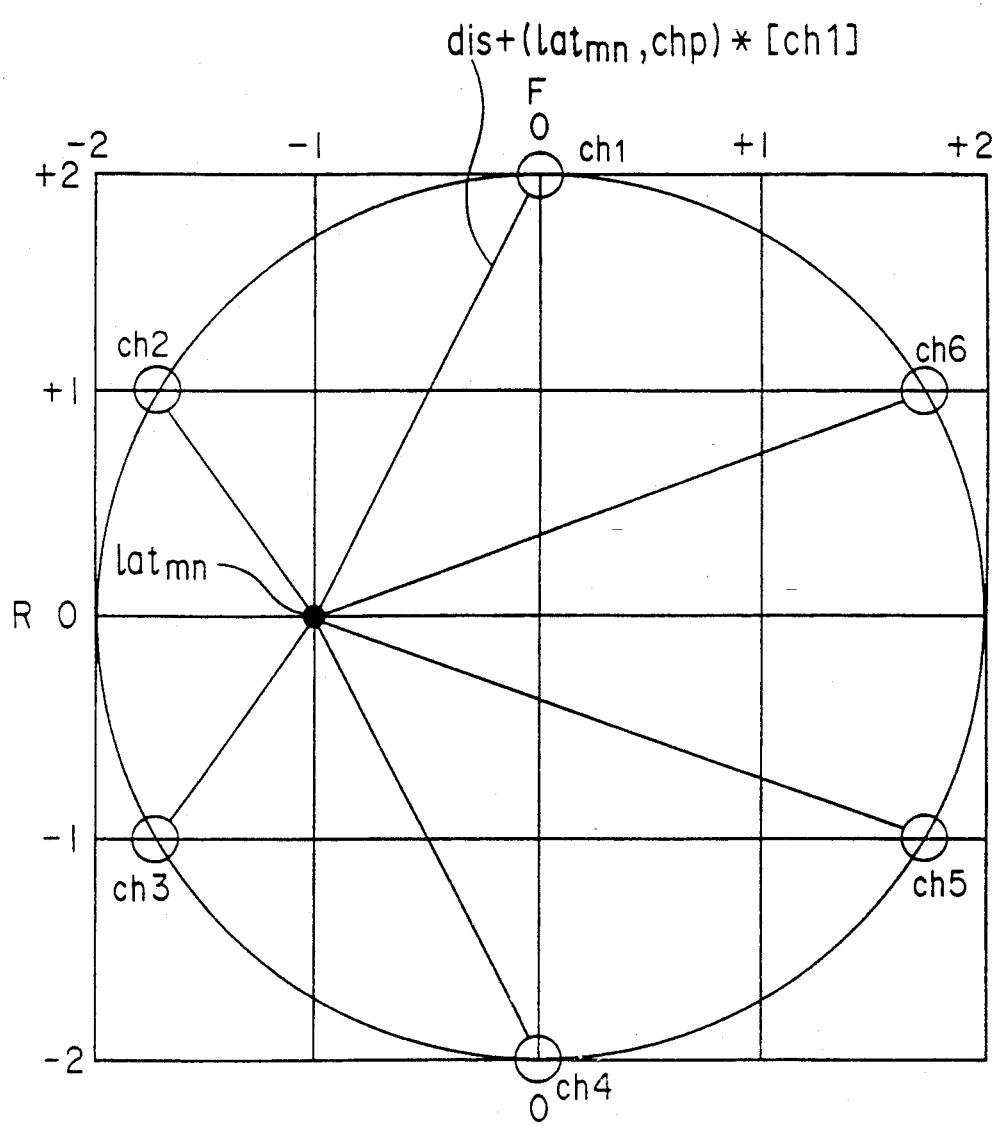
FIG. 11 is a diagram illustrating the concept of 6-point input and lattice.

FIG. 11 shows the concept of 6-point inputs and lattice. In the embodiment shown in the figure, a large circle is assumed to represent the cross section of a head, on which six sensors are disposed. In the figure, symbol F indicates the front, R the right side, L the left side, and O the rear of the head. In addition, a square is assumed to be circumscribed about or around the large circle at F, R, L and O.

The circumscribed square is equally divided into 16 (16 points), and a number from $-2$ to 2 is given to each of the longitudinal and lateral lattices. Using the lattice numbers, each lattice point is expressed by the lattice point (m, n). m and n here are integers from $-2$ to 2; m being the lateral (R-L) number, and n the longitudinal (F-O) number.

To obtain a 6-point input, six sensors (channels) are installed on the head of a subjected, as shown in the figure. The relative positions of channels and lattices are such as shown in the figure. Assume that a value (measured value) at a certain channel ch p (p is any of integers from 1 to 6 representing a channel number) is expressed by [ch p].

Assume that a certain lattice point (m, n) is expressed by lat m n, and the distance between the lattice point and a certain channel ch p is expressed by dist (lat m n, ch p). The effect of a certain channel ch p on a certain lattice point lat m n is dependent on dist (lat m n, ch p)*[ch p]. Consequently, the lat m n value [lat m n] determined by [ch p] is expressed by $$[lat\ mn] \sum_{p=1}^{p} \frac{dist(lat\ mn, ch\ p)*[ch\ p]}{\sum_{p=1}^{p} dist(lat\ mn, ch\ p)}$$

taking into account the effect of all channels ch p on the lattice point lat m n.

Figure 12:
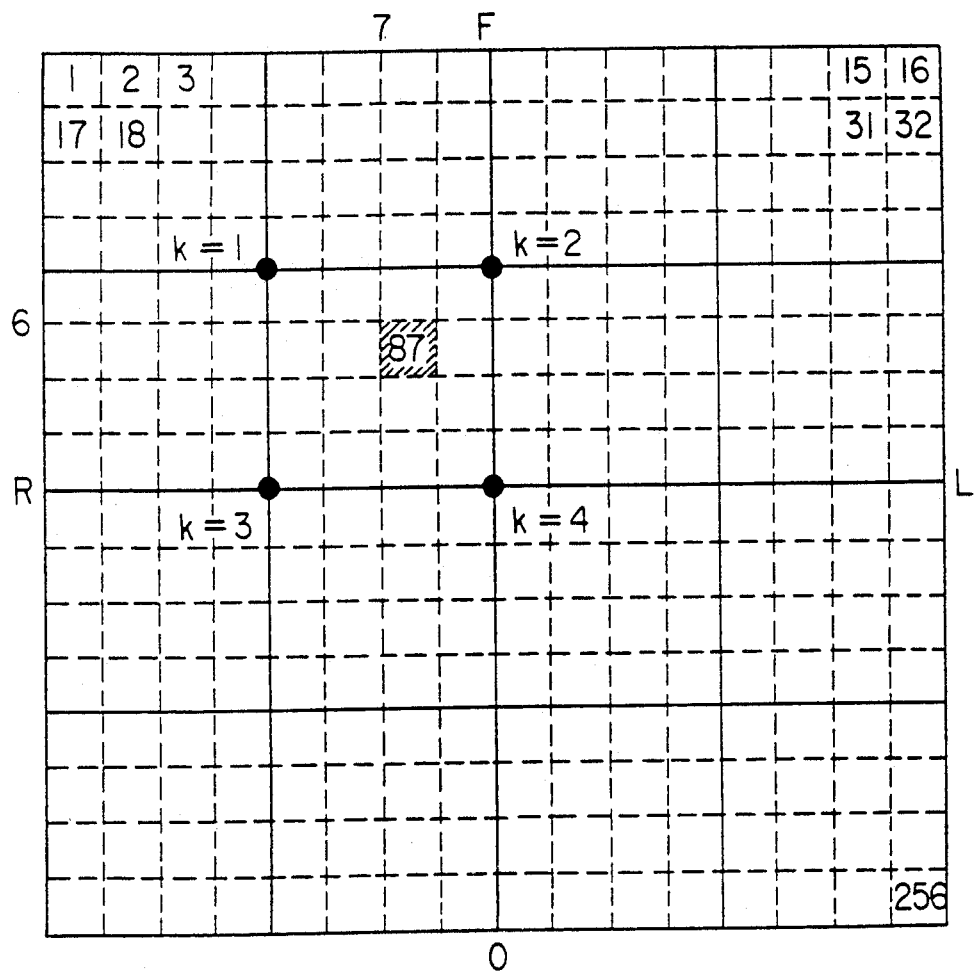
FIG. 12 is a diagram illustrating the concept of tiles.
Figure 13A:
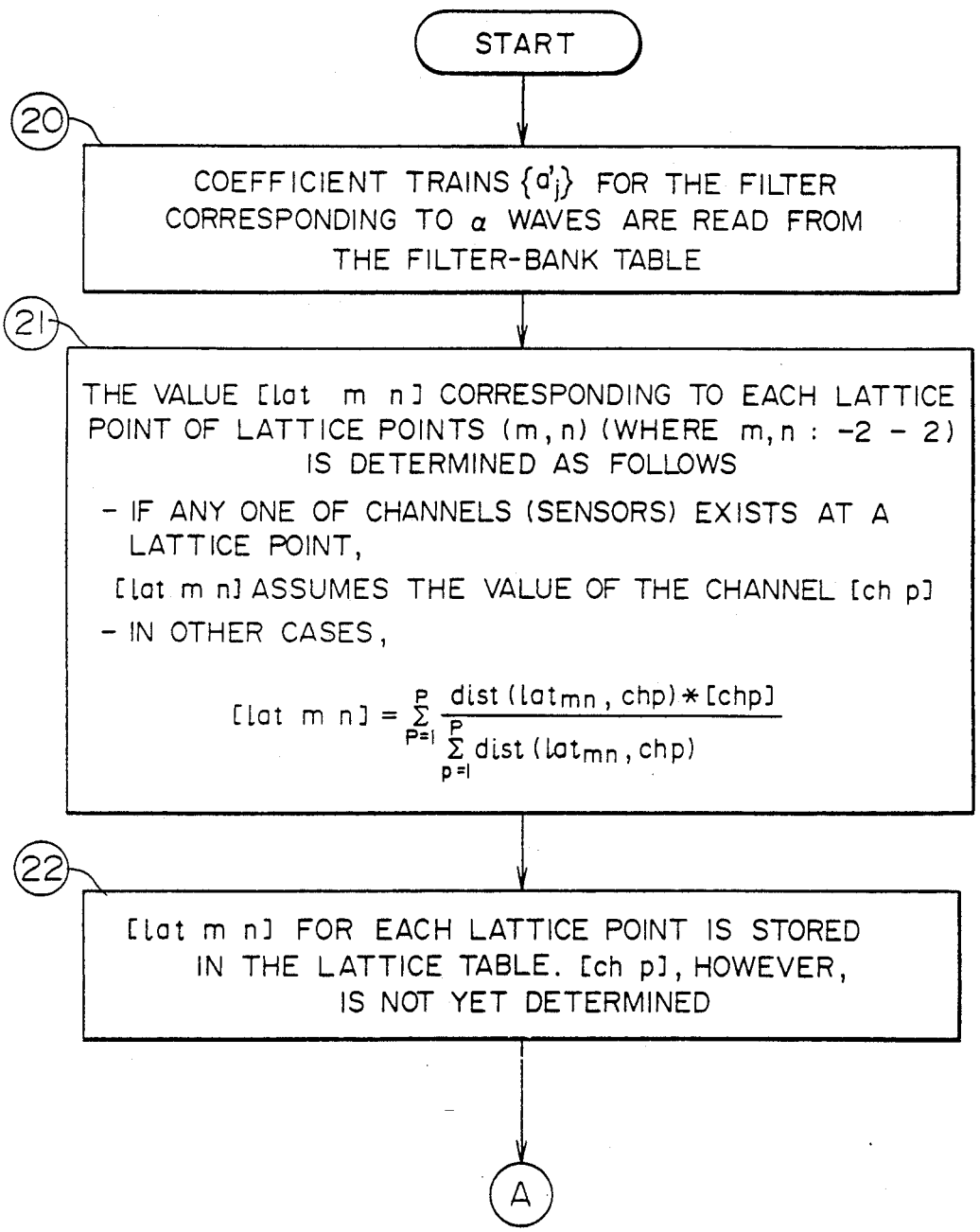
FIGS. 13 A-D are a flow chart showing the details of display processing.
Figure 13B:
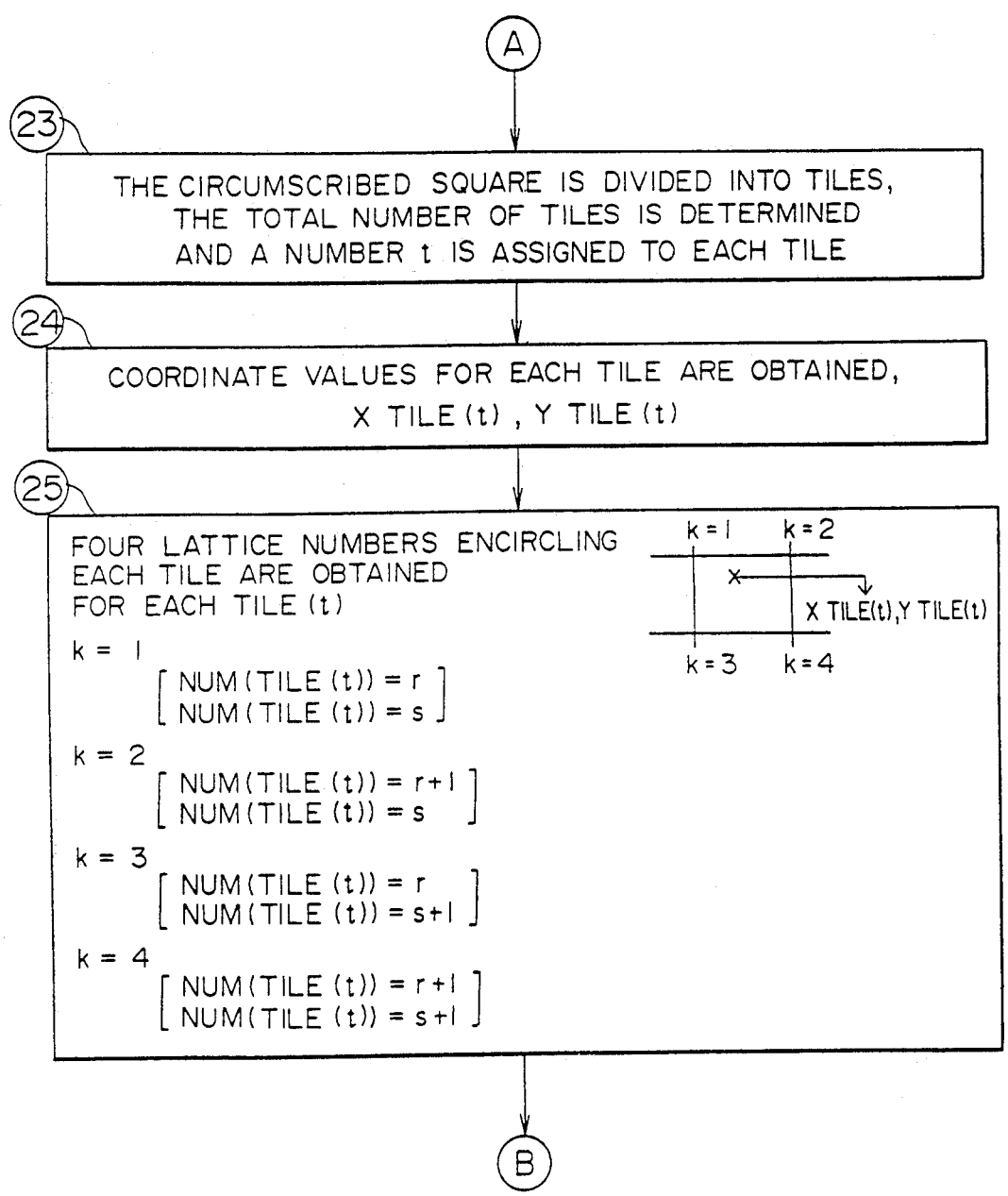
Figure 13C:
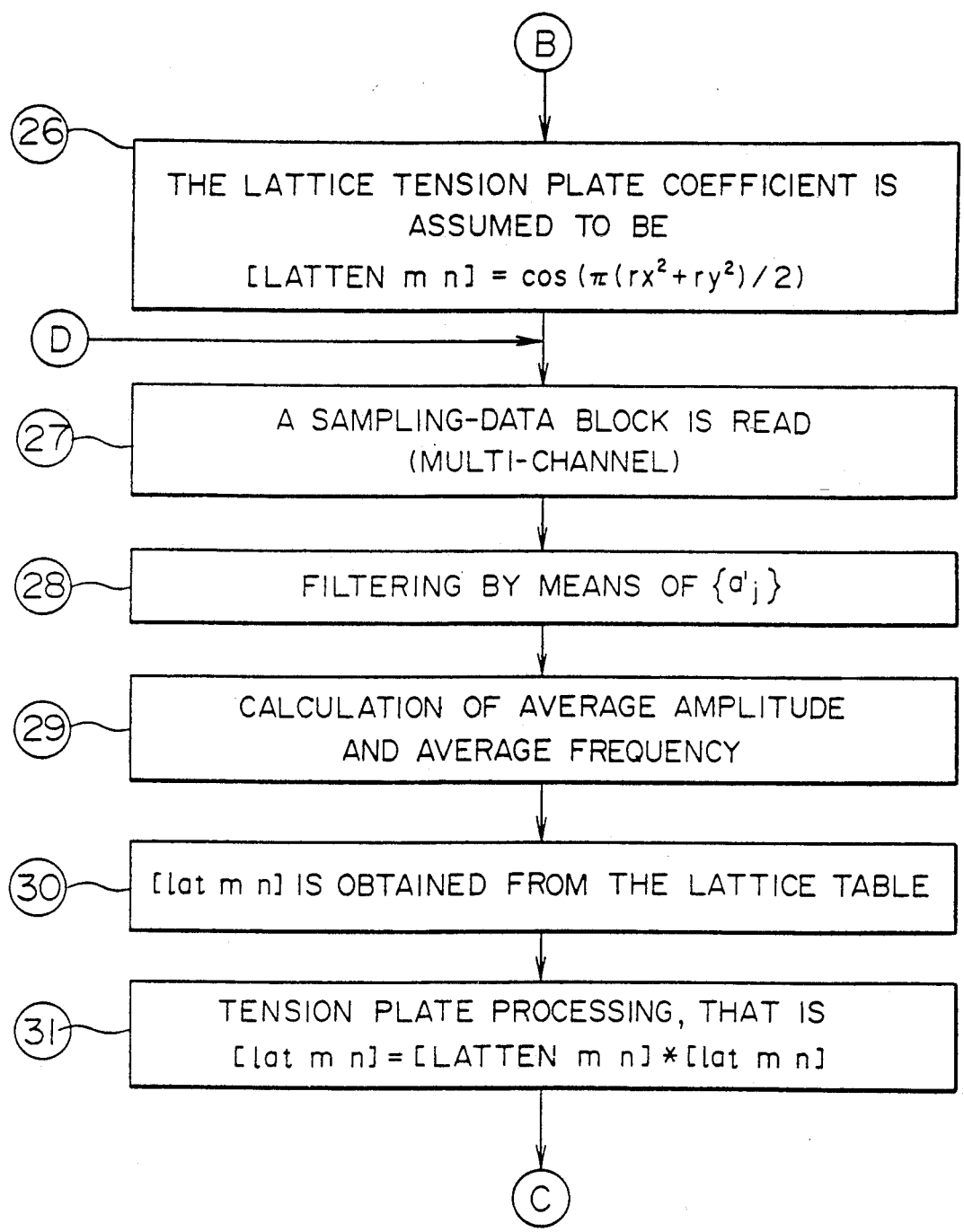
Figure 13D:
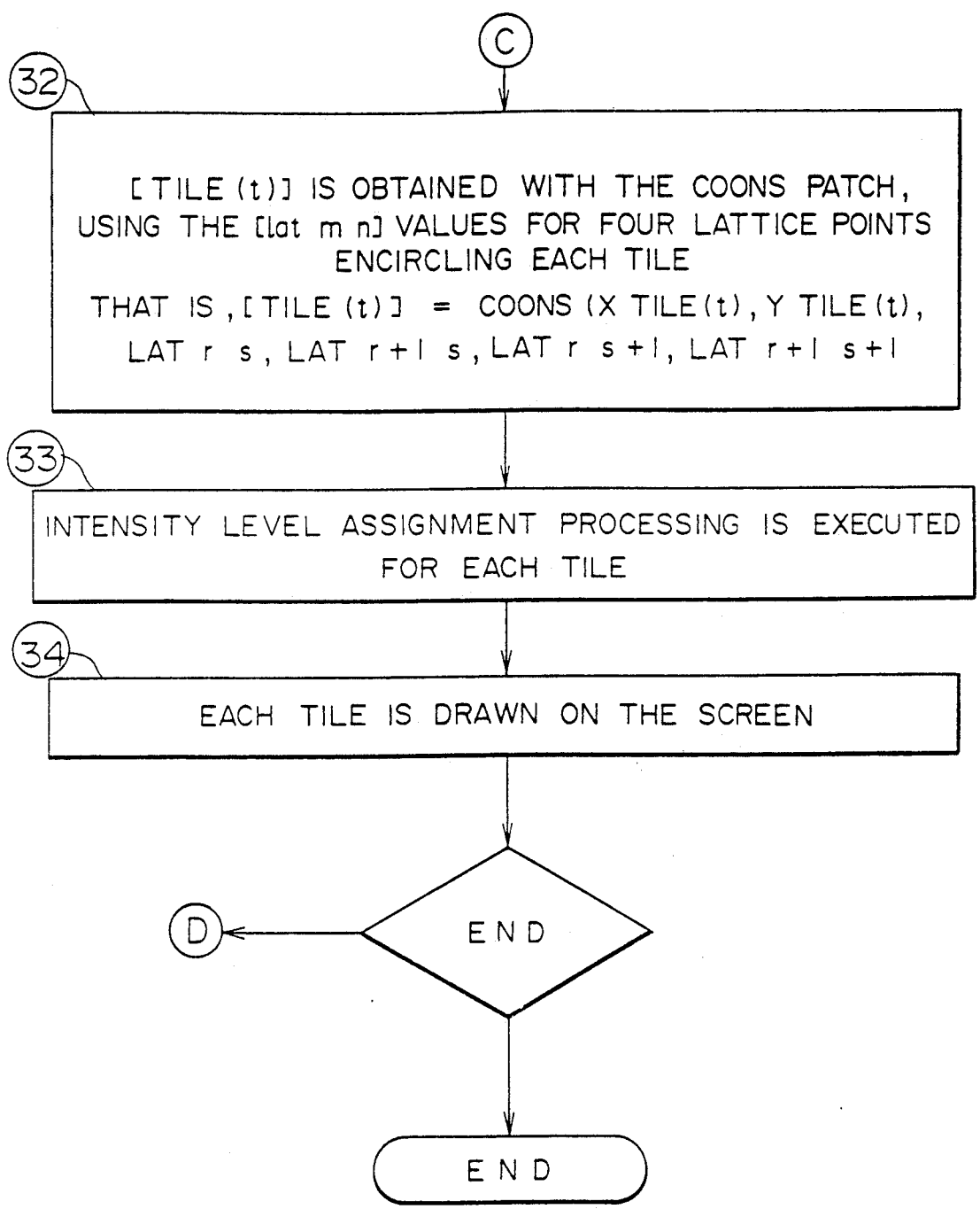
Figure 14:
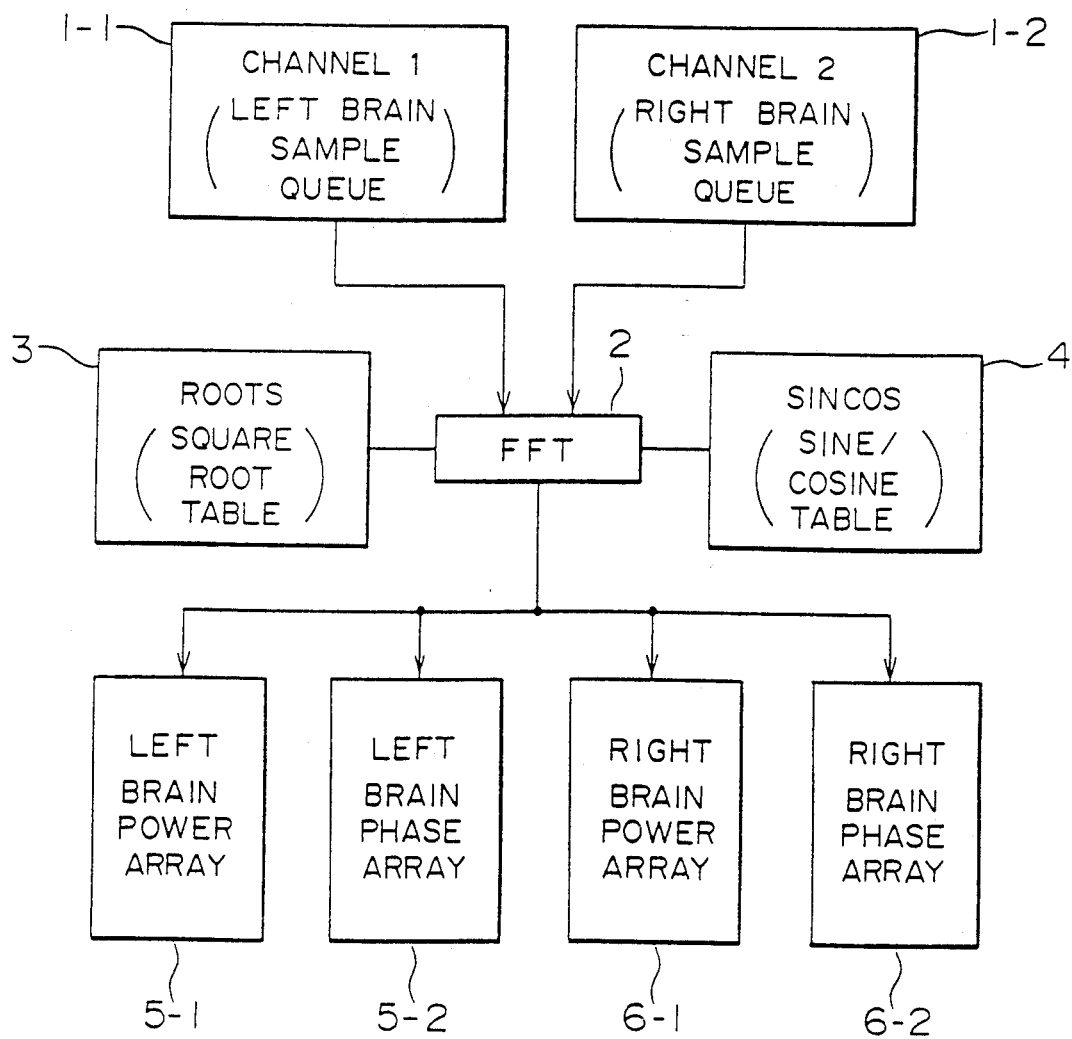
FIG. 14 shows the construction of the conventional FFT processing.

FIG. 12 shows the concept of tiles introduced in this embodiment. In the embodiment shown in the figure, the square circumscribed about the large circle shown in FIG. 12 is equally divided into 256, each of which is called a tile. The square may be divided into tiles in such a manner as to cause a tile to overlap any of the lattices, and tiles need not be of a square shape.

Each tile is given a number t (1, 2, 3, - - - ) sequentially, as shown in the figure. The X cordinates of the tile having a number t are expressed by X tile(t), the Y cordinates thereof by Y tile(t). In the figure, the cordinates of the 87th tile (expressed as tile (87)) are X tile (87)=7, Y tile (87))=6.

In the embodiment shown in the figure, four lattice points (lat m n) encircling the tile (87) are determined. The lattice points having such relative positions as shown in the figure with respect to the tile (87) are distinguished by giving values from k=1 to 4.

Now, assuming that the numbers of a lattice point lat m n having a relative position of k=1 (on the F side and the R side of a tile (t) with respect to the tile (87) are expressed as num (tile (t))=r (=m), num (tile (t))=s (=n), the lattice point having a relative position of k=2 can be expressed as num (tile (t))=r+1 num (tile (t))=s, the lattice point having a relative position of k=3 can be expressed as num (tile (t))=r num (tile (t))=s+1, and the lattice point having a relative position of k=4 can be expressed as num (tile (t))=r+1 num (tile (t))=s+1.

Here, num (tile (t)) is a number closest to the tile among the lat m n values satisfying each of the relations k=1-4. When k=1 for tile (t), for example, the numbers m and n closest to the tile (t) among one or multiple lat m n values on the F side and the R side of the tile (t) are determined as num (tile (t))=r and num (tile (t))=s.

When four lattice points encircling a given tile (t) are obtained in this way, the value [tile (t)] for the tile (t) can be obtained from the four lattice point values [lat m n] using the Coons patch. That is, [tile (t)]=Coons (X tile (t), Y tile (t), lat r s, lat r+1 s, lat r s+1, lat r+1 s+1). If the numbers of lat r s are known, the X and Y cordinates thereof can be obtained easily, as is evident from FIG. 13.

FIG. 13 is a flow chart specifically illustrating proceedings (9) through (13) in the processing flow shown in FIG. 8 that is for displaying the chart shown in FIG. 7.

Processing (20): A coefficient train $\{a'_j\}$ for filters (bandwidth: 7.5 Hz-13.5 Hz) corresponding to $\alpha$ waves is read from the filter-bank table. The coefficient train $\{a'_j\}$ is determined in advance, taking into account the properties of the filters.

Processing (21): The value [lat m n] corresponding to each of the lattice points (m, n) shown in FIG. 11 is determined. If one channel (sensor) ch p exists in a lattice point, the value ]lat m n] at that time is set at the channel value [ch p] itself. In other cases, the value [lat m n] can be obtained from the six channel values, and expressed by the following equation.

$$[lat\ mn] \sum_{p=1}^{p} \frac{dist(lat\ mn,\ ch\ p)*[ch\ p]}{\sum_{p=1}^{p} dist(lat\ mn,\ ch\ p)}$$

Processing (22): The value [lat m n] for each lattice point is stored in the lattice table. At this moment, however, [ch p] is not yet determined.

Processing (23): As shown in FIG. 12, the square circumscribed about the cross section of the head is divided into tiles, the total number of tiles is obtained, and a number t is given to each tile.

Processing (24): The X cordinates X tile (t) and the Y cordinates Y tile (t) for each tile are obtained.

Processing (25): The lattice numbers of four lattice points encircling each tile are obtained. As described above, the lattice numbers of the four lattice points for the tile (t) are; for the lattice point having a relative position of k=1, num (tile (t))=r num (tile (t))=s for the lattice point having a relative position of k=2, num (tile (t))=r+1 num (tile (t))=s for the lattice point having a relative position of k=3, num (tile (t))=r num (tile (t))=s+1 and for the lattice point having a relative position of k=4, num (tile (t))=r+1 num (tile (t))=s+1

Processing (26): Taking into account weights to allow for values at adjacent lattice points for each lattice point (lat m n), the lattice tension plate coefficient latten m n is set to latten m n=$\cos(\pi(r_x^2+r_y^2)/2)$. $r_x$ here is the distance in the horizontal direction from m, $r_y$ is the distance in the vertical direction from n.

Processing (27): The sampling-data block $\{x_i\}$ from a sensor is read.

Processing (28): The read sampling-data block $\{x_i\}$ is subjected to filtering processing in the filter (bandwidth: 7.5 Hz-13.5 Hz) corresponding to $\alpha$ waves, using the coefficient train that was previously read in Processing (20). ($\{y_i\}$ is obtained in the same manner as that with FIG. 10.)

Processing (29): The average amplitude and average frequency for the obtained $\{y_i\}$ are obtained through calculation.

Processing (30): The value [lat m n] for each lattice point that was previously stored in Processing (22)

is written from the lattice table. [lat m n] is obtained by introducing the average amplitude of {$y_i$} obtained in Processing (29) into the [ch p] value in the [lat m n] value.

Processing (31): Tension plate processing is carried out for each lattice point. That is, the value latten m n* [lat m n] obtained by multiplying the [lat m n] obtained in Processing (30) by the lattice tension plate coefficient obtained in Processing (26) is used a new [lat m n] value. Thus, the [lat m n] value for each lattice point is corrected by the lattice tension plate coefficient.

Processing (32): The [tile (t)] value for each tile is obtained with the Coons patch, using the [lat m n] values for four lattice points encircling each tile. The four lattice points encircling each tile have the lattice numbers obtained in Processing (25); that is, lat r s, lat r+1 s, lat r s+1, and lat r+1 s+1. These [lat m n] values are those values corrected in Processing (31). The [tile (t)] value for a tile (t), encircled by them, with the X cordinates being X tile(t) and Y cordinates Y tile(t) can be obtained with the Coons patch using the value for each lattice point and the distances between the tile and the lattice points, and unilaterally determined.

Processing (33): Each tile is subjected to intensity-level assigning, using the [tile (t)] value for the tile (t) obtained in Processing (32).

Processing (34): Topographic representation is carried out by producing the image of each tile on the display screen in accordance with the intensity-levels assigning results.

Check is then made to see if processing is completed for all the sampling-data block. If not completed, Processing (27) and the thereafter are repeated.

As described above, this invention makes real-time display possible by using digital filters, and also makes it possible to perform real-time processing with a small computer by simplifying processing for obtaining topography.

What is claimed is:

1. A biological signal processing system comprising:
   a first sensor generating a signal representative of brian waves of a human being;
   a second sensor generating a signal representative of other brian waves of a human being;
   a differential amplifier means for generating a differential signal representing a difference between the signals of said first and second sensors;
   a lowpass filter means for substantially removing frequency portions of the differential signal above an upper cutoff frequency of 30.5 Hz;
   a highpass filter means for substantially removing frequency portions of the differential signal below a lower cutoff frequency of 0.5 Hz;
   sample means for sampling the differential signal after it has been acted on by said lowpass filter means and said highpass filter means and for forming a data signal in a plurality of time spans;
   a plurality of digital filter means, each of said plurality of digital filter means receiving the data signal from said sample means, said each digital filter means removing portions of the data signal above and below a bandwidth of 1 Hz, said each digital filter means having a respective bandwidth positioned at a different spectral location and delivering a filter signal predominately emphasizing said bandwidth of said each digital filter means; and
   display means for receiving the filter signals from said each digital filter means and separately displaying a magnitude of each of said filter signals.

2. A biological signal processing system as set forth in claim 1 wherein the magnitudes of said filter signals are displayed in the form of histograms.

3. A biological signal processing system as set forth in claim 2 wherein, together with said histograms, a ratio of the magnitude of an α wave signal component extracted from the filter signals to the filter signals remaining after the extraction is displayed.

4. A biological signal processing system as set forth in claim 1 wherein said filter signals are expressed in a time series, and the magnitudes of said filter signals are expressed in grades.

5. A biological signal processing system as set forth in claim 1 wherein predetermined frequency components of the filter signals are displayed in the form of topography.

6. A biological signal processing system as set forth in claim 5 wherein said predetermined frequency components are α waves.

7. A biological signal processing system comprising:
   a first sensor generating a signal representative of brian waves of a human being;
   a second sensor generating a signal representative of other brian waves of a human being;
   a differential amplifier means for generating a differential signal representing a difference between the signals of said first and second sensors;
   a lowpass filter means for substantially removing frequency portions of the differential signal above an upper cutoff frequency of 30.5 Hz;
   a highpass filter means for substantially removing frequency portions of the differential signal below a lower cutoff frequency of 0.5 Hz;
   sample means for sampling the differential signal into sample blocks ($x_i$) after it has been acted on by said lowpass filter means and said highpass filter means, and for forming a data signal in a plurality of time spans;
   a plurality of digital filter means, each of said plurality of digital filter means receiving the data signal from said sample means, said each digital filter means removing portions of the data signal above and below a bandwidth, said each digital filter means having a respective bandwidth positioned at a different spectral location and delivering a filter signal predominately emphasizing said bandwidth of said each digital filter means, and said each digital filter means including a coefficient train ($a_j$) removing the portions above and below a respective bandwidth, said each digital filter means calculating an instantaneous power spectrum (ppow) by $$y_i = \sum_{j=-n}^{n} a_j x_{i-j}$$

said digital filter then calculating a power pow(k) by $$pow(k) = \Sigma y_i = \sum_{i=din}^{(2l+1)-din} y_i$$

a present power pow'(k) is then obtained by forming a time series of said power pow(k) and multiplying said time series of said power pow(k) by weight-average window function coefficients wcof(i'), where $$wcof(i') = cos(\pi/2w \cdot i')$$

(i' = 1, 2, --- w); and display means for receiving the filter signals from said each digital filter means and separately displaying a magnitude of each of said filter signals.

8. A biological signal processing system in accordance with claim 7, wherein:

said bandwidth of said each digital filter means is approximately 1 Hz and spaced substantially continuously from approximately 0.5 to 30.5 Hz.

9. A biological signal processing system comprising:

a sensor generating a sensor signal corresponding to biological signals;

sample means for sampling the sensor signal and for forming a data signal in a plurality of time intervals;

a plurality of filter means, each of said plurality of filter means receiving the data signal from said sample means, said each filter means removing portions of the data signal above and below a bandwidth for each time interval, said each filter means having a respective bandwidth positioned at a different spectral location and delivering a filter signal predominately emphasizing said bandwidth of said each filter means for each time interval;

analysis means for performing a frequency analysis on the filter signal of said each filter means for each time interval by using interval integral calculus; and display means for displaying the frequency analysis of said each filter means and separately displaying a magnitude of each of said filter signals.

* * * * *